(12) United States Patent
Linden

(10) Patent No.: US 10,969,333 B2
(45) Date of Patent: Apr. 6, 2021

(54) SENSING CANNABIS AND OPIOIDS IN EXHALED BREATH BY INFRARED SPECTROSCOPY

(71) Applicant: N2 Biomedical LLC, Bedford, MA (US)

(72) Inventor: Kurt J. Linden, Wayland, MA (US)

(73) Assignee: VOX BIOMEDICAL LLC, Bedford, MA (US)

( * ) Notice: Subject to any disclaimer, the term of this patent is extended or adjusted under 35 U.S.C. 154(b) by 0 days.

(21) Appl. No.: 16/043,246

(22) Filed: Jul. 24, 2018

(65) Prior Publication Data

US 2019/0041321 A1 Feb. 7, 2019

Related U.S. Application Data

(60) Provisional application No. 62/540,115, filed on Aug. 2, 2017.

(51) Int. Cl.
*G01J 5/02* (2006.01)
*G01N 21/3504* (2014.01)
(Continued)

(52) U.S. Cl.
CPC ......... *G01N 21/3504* (2013.01); *A61B 5/097* (2013.01); *A61B 5/4845* (2013.01);
(Continued)

(58) Field of Classification Search
CPC ...... G01N 21/81; G01N 33/497; G01N 21/35; G01N 2201/0221; G01N 21/3554;
(Continued)

(56) References Cited

U.S. PATENT DOCUMENTS 6,555,821 B1 4/2003 Himberg et al.
2005/0150385 A1* 7/2005 Huang ................. A41D 13/11
96/69
(Continued)

FOREIGN PATENT DOCUMENTS

EP 0897708 A2 * 2/1999 ............ A61J 1/2089
EP 0897708 A2 2/1999

OTHER PUBLICATIONS

Ohta et al., "Studies on Fentanyl and related compounds IV. chromatographic and spectrometric discrimination of Fentanyl and its derivatives," Aug. 1999, Journal of Analytical Toxicology, vol. 23, pp. 280-295. (Year: 1999).*

(Continued)

*Primary Examiner* — Kiho Kim
(74) *Attorney, Agent, or Firm* — Hunter Clark PLLC

(57) ABSTRACT

Techniques for detecting narcotics such as tetrahydrocannabinol (THC) or other aerosols such as cannabinoids, opioids, etc., in an exhaled breath using infrared spectroscopy are provided. An example of an apparatus for sensing THC according to the disclosure includes a tunable laser source, at least one photodetector, a sample cell disposed between the tunable laser source and the at least one photodetector, and at least one processor operably coupled to the tunable laser source and the at least one photodetector and configured to provide a control signal to the tunable laser source, determine a spectral absorption line or group of absorption lines associated with THC based on an intensity of infrared light detected by the at least one photodetector, and determine a THC concentration value based on the spectral absorption line intensity. A laser-based apparatus for sensing narcotics in exhaled breath may include a single, dual, or multi-optical frequency comb spectrometer.

16 Claims, 10 Drawing Sheets

(51) Int. Cl.

| | | |
|---|---|---|
| *G01N 21/39* | (2006.01) | |
| *G01N 33/497* | (2006.01) | |
| *G01N 21/00* | (2006.01) | |
| *G01N 33/487* | (2006.01) | |
| *G01N 21/35* | (2014.01) | |
| *G01N 21/31* | (2006.01) | |
| *A61B 5/097* | (2006.01) | |
| *A61B 5/00* | (2006.01) | |
| *A61B 5/145* | (2006.01) | |

(52) U.S. Cl.
CPC .............. *G01N 21/00* (2013.01); *G01N 21/31* (2013.01); *G01N 21/35* (2013.01); *G01N 21/39* (2013.01); *G01N 33/487* (2013.01); *G01N 33/497* (2013.01); *A61B 5/14507* (2013.01); *G01N 2021/3595* (2013.01); *G01N 2201/1235* (2013.01)

(58) Field of Classification Search
CPC ....... G01N 2001/007; G01N 2001/022; G01N 2001/4061; G01N 2021/399; G01N 21/3504; G01N 21/39; G01N 2201/399; G01N 2201/0612; G01N 2201/0697; G01N 2201/1235; G01N 21/00; G01N 21/31; G01N 33/487; G01N 2021/3595; G01N 2021/1235; A61B 5/097; A61B 5/4845; A61B 5/14507
See application file for complete search history.

(56) References Cited

U.S. PATENT DOCUMENTS

| | | | | |
|---|---|---|---|---|
| 2010/0159575 | A1* | 6/2010 | Chen .................... | G01N 33/497 435/287.2 |
| 2011/0170098 | A1* | 7/2011 | Normand .................. | G01J 3/28 356/327 |
| 2012/0133931 | A1 | 5/2012 | Fermann et al. | |
| 2012/0212735 | A1 | 8/2012 | Palmskog et al. | |
| 2013/0006068 | A1* | 1/2013 | Gemer ................ | A61B 10/0051 600/314 |
| 2014/0288454 | A1* | 9/2014 | Paz ...................... | A61B 5/4845 600/532 |
| 2015/0233762 | A1 | 8/2015 | Goldring et al. | |
| 2015/0298069 | A1* | 10/2015 | Bae ......................... | C08L 81/06 210/500.27 |
| 2016/0061807 | A1* | 3/2016 | Ravishankar ........ | G01N 33/487 506/6 |
| 2016/0139055 | A1 | 5/2016 | Pierce, III et al. | |
| 2016/0299061 | A1* | 10/2016 | Goldring ............... | G01J 3/0275 |

OTHER PUBLICATIONS

Sigma-Aldrich Production information, "Oxycodone hydrochloride solution", 2015, available online at www.sigmaaldrich.com/content/dann/sigma-aldrich/docs/sigma-aldrich/datasheet/1/02628-slbn2071vdat.pdf, 2 pages. (Year: 2015).*
Sigma Product Information, "9-Tetrahydrocannabinol", 2004,available online at www.sigmaaldrich.com/content/dam/sigma-aldrich/docs/sigma-aldrich/datasheet/1/t4764-091k8801dat.pdf, 2 pages. (Year: 2004).*
Bartels et al., "10-GHz self-referenced optical frequency comb," Oct. 30, 2009, Science, vol. 326, two pages. (Year: 2009).*
CDCNCHS, Underlying Cause of Death, wonder.cdc.gov; 1999-2016 Results Form pp. 1-4.
Florence et al., The Economic Burden of Prescription Opioid Overdose, Abuse and Dependence in the United States, 2013, HHS Public Access, Med Care, PMC 2018, pp. 1-14.
Cicero et al., The Changing Face of Heroin Use in the United States, JAMA Psychiatry, Jul. 2014, vol. 71, No. 7, pp. 821-826.
NIDA, Medications to Treat Opioid Use Disorder, Jun. 2018, www.drugabuse.gov, pp. 1-47.
Law, et al., Analyticala Methodology and Assessment of Potential Second-Hand Exposure to Fentanyl in the Hospital Setting, Journal of Addictive Diseases, vol. 29, 2010, Issue 1, Abstract.
Beck, et al., Determination of Amphetamine and Methylphenidate in Exhaled Breath of Patients Undergoing ADHD Treatment, Ther Drug Monit, 2014, pp. 1-7.
Milone, Laboratory Testing for Prescription Opioids, J. Med. Toxicol, 2012, vol. 8, pp. 408-416.
Xi, et al., Detecting Lung Diseases from Exhaled Aerosols: Non-Invasive Lung Diagnosis Using Fractal Analysis and SVM Classification, PLOS One, 2015, pp. 1-19.
Linden, Driver Breath Measurement of Marijuana Intoxication by Infrared Spectroscopy, Submitted to U.S. Dept. of Transportation SBIR Program, 2017, pp. 1-33.
Worle, et al., Breath Analysis With Broadly Tunable Quantum Cascade Lasers, Analytical Chemistry, 2013, vol. 85, pp. 2697-2702.
Ye, et al., Sparse Methods for Biomedical Data, NIH Public Access, SIGKDD Explor: Author Manuscript, 2013, pp. 1-24.
Kallet, The Role of Inhaled Opioids and Furosemide for the Treatment of Dyspnea, Respiratory Care, Jul. 2007, vol. 52, No. 7, pp. 900-910.
Sigma-Aldrich Co. LLC, Delta-9-Tetrahydrocannabinol Methanol Solution, www.sigmaaldrich.com, Prouct Information, 2004.
Sigma-Aldrich Co. LLC, Oxycodone Hydrochloride Solution, www.sigmaaldrich.com, Product Information, 2015.
Ohta et al., Studies on Fentanyl and Related Compounds IV, Journal of Analytical Toxicology, vol. 23, Jul./Aug. 1999, pp. 280-285.
The Recovery Village, How Do I Know if Someone is on Opiates?, www.therecoveryvillage.com/opiate-addiction, pp. 1-7, Jul. 19, 2018.
Beck, et al., Study of the Sampling of Methadone From Exhaled Breath, PMID: 21619719, Indexed for Medline, J. Anal. Toxicol. Jun. 2011; 35(5) 257-63.
Yan, et al., Infectious Virus in Exhaled Breath of Symptomatic Seasonal Influenza Cases From a College Community, www.pnas.org/cgi/doi pp. 1-10, PNAS Early Edition, Dec. 15, 2017.
Bruker, Advertisement for Company Products, Applications, Service, News Events Jul. 19, 2018.
NIST Chemistry WebBook, NIST Standard Reference Database No. 69, Jun. 21, 2017.
Matteo, et al., Analysis of Functional Groups in Atmospheric Aerosols by Infrared Spectroscopy, Infoscience, EPFL Scientific Publications, Oct. 14, 2016.
Foral, et al., Nebulized Opioids Use in COPD, Abstract, PubMed.gov, Chest. Feb. 2004; 125(2): 691-4.

* cited by examiner

SENSING CANNABIS AND OPIOIDS IN EXHALED BREATH BY INFRARED SPECTROSCOPY

CROSS-REFERENCE TO RELATED APPLICATIONS

This application claims the benefit of U.S. Provisional Application No. 62/540,115 filed Aug. 2, 2017, entitled "TETRAHYDROCANNABINOL SENSING IN EXHALED BREATH BY INFRARED SPECTROSCOPY," the entire contents of which is hereby incorporated herein by reference.

BACKGROUND

The increasing use of narcotics such as opioids and marijuana is creating severe issues for medical and law enforcement organizations. The misuse of and addiction to opioids, including prescription pain relievers, heroin, and synthetic opioids such as fentanyl, presents a global crisis that affects public health as well as social and economic welfare. The legalization of marijuana is also creating issues for law enforcement officials that are tasks with ensuring public safety.

Simulator and laboratory studies have found that delta-9-tetrahydrocannabinol (THC) is the chemical primarily responsible for most of marijuana's psychological effects, and that it is this chemical that is associated with intoxication resulting in impairment of memory, coordination and time perception, leading to potentially dangerous behavior such as diminished automobile driver performance. According to the National Institute on Drug Abuse (NIDA) this chemical acts much like the cannabinoid chemicals made naturally by the human body. Cannabinoid receptors are concentrated in certain areas of the brain associated with thinking, memory, pleasure, coordination and time perception. According to NIDA documents, THC attaches to these receptors and activates them and thereby affects a person's memory, pleasure, movements, thinking, concentration, coordination, and sensory and time perception. THC is one of many chemical compounds found in the resin secreted by glands of the marijuana plant. More of these glands are found around the reproductive organs of the plant than on any other area of the plant. Other compounds unique to marijuana, called cannabinoids, are also present in this resin. Among the reasons for increasing public support for the legalized use of marijuana is the fact that studies have shown that cannabinoids downregulate cytokine and chemokine production and, in some models, upregulate T-regulatory cells (Tregs) as a mechanism to suppress inflammatory response. The endocannabinoid system is also involved in immunoregulation. For example, administration of endocannabinoids or use of inhibitors of enzymes that break down the endocannabinoids, has been shown to result in immunosuppression and recovery from immune-mediated injury to organs such as the liver. Manipulation of endocannabinoids and/or use of exogenous cannabinoids in vivo can constitute a potent treatment modality against inflammatory disorders. There is strong evidence supporting the potential use of cannabinoids as a new class of anti-inflammatory agents against a number of inflammatory and autoimmune diseases that are primarily triggered by activated T-cells or other cellular immune components. Because of these and a range of other apparently beneficial medicinal effects of marijuana, it can be expected that continued public advocacy for legalization of marijuana will eventually result in its widespread use. This will pose an ever increasing problem for public safety and law enforcement officials. In addition to THC, other intoxicating and mind-altering narcotics including opioids are known to be contained in the exhaled breath of users in the form of aerosols. These mind-altering narcotics also pose potentially serious safety hazards among their users, and are therefore of great interest in being capable of being detected in the exhaled breath of their users.

SUMMARY

An example of a method of sensing a narcotic in exhaled breath according to the disclosure includes receiving a breath input from a test subject with a filter material, disposing the filter material in an optical path between a laser source and a photodetector, detecting an intensity of infrared light that traverses the filter material with the photodetector, determining one or more spectral absorption lines associated with the narcotic based on the intensity of the infrared light as a function of photon energy, determining a narcotic concentration value based on the one or more spectral absorption lines, and outputting the narcotic concentration value.

Implementations of such a method may include one or more of the following features. The laser source may be a tunable quantum cascade laser. The laser source may be an optical frequency comb laser. The laser source may be a tunable laser such as a diode laser, a quantum cascade laser, a solid-state laser, a gas laser or other type of laser whose output optical frequency can be electronically or mechanically controlled. Receiving the breath input from the test subject may include providing the test subject a breath sampler device comprising a tube and the filter material. The narcotic may be tetrahydrocannabinol (THC) and the one or more spectral absorption lines associated with THC may include a spectral absorption line at approximately 1036.94 cm-1. The narcotic may be oxycodone and the one or more spectral absorption lines associated with oxycodone may be approximately between 700-1500 cm-1. The narcotic may be fentanyl and the one or more spectral absorption lines associated with fentanyl may be approximately between 600-1500 cm-1. The narcotic may be morphine and the one or more spectral absorption lines associated with morphine may be approximately between 600-1130 cm-1. The narcotic may be tetrahydrocannabinol (THC) and the one or more spectral absorption lines associated with THC may be approximately between 600-1700 cm-1. The one or more spectral absorption lines may include one or more spectral absorption lines known to be associated with Cannabidiol (CBD). The filter material may be a gas filter material. The gas filter material may be a Luer filter. The filter material may include a liquid filter material. The filter material may include a solid filter material.

An example of an apparatus for sensing a narcotic in an exhaled breath according to the disclosure includes a tunable laser source, at least one photodetector, a sample cell disposed between the tunable laser source and the at least one photodetector, and at least one processor operably coupled to the tunable laser source and the at least one photodetector and configured to provide a control signal to the tunable laser source, determine one or more spectral absorption lines associated with the narcotic based on an intensity of infrared light detected by the at least one photodetector, and determine a narcotic concentration value based on the spectral absorption lines.

Implementations of such an apparatus may include one or more of the following features. The tunable laser source may be a tunable quantum cascade laser. The tunable laser source may operate as an optical frequency comb laser. The tunable laser source may include one of a diode laser, a solid-state laser, a gas laser, other type of laser whose output optical frequency can be electronically or mechanically controlled. The apparatus may include a separate breath sampler device including a tube and a filter material configured to receive a breath input from a test subject. The at least one processor may be configured to determine the one or more spectral absorption lines is associated with THC as approximately 1036.94 cm-1. The at least one processor may be configured to determine the one or more spectral absorption lines known to be associated with THC. The narcotic may be oxycodone and the at least one processor may be configured to determine the one or more spectral absorption lines associated with oxycodone are approximately between 700-1500 cm-1. The narcotic may be fentanyl and the at least one processor may be configured to determine the one or more spectral absorption lines associated with fentanyl are approximately between 600-1500 cm-1. The narcotic may be morphine and the at least one processor may be configured to determine the one or more spectral absorption lines associated with morphine are approximately between 600-1130 cm-1. The sample cell may include a filter material. The filter material may be a Luer filter.

An example of a method for sensing a narcotic in an exhaled breath according to the disclosure includes spectroscopically detecting the narcotic contained in the exhaled breath of a test subject by infrared spectroscopy using a Fourier Transform InfraRed (FTIR) interferometer.

An example of a method for sensing a narcotic in an exhaled breath according to the disclosure includes spectroscopically detecting the narcotic contained in the exhaled breath of a test subject by infrared spectroscopy using a tunable quantum cascade laser.

An example of a method for sensing a narcotic in an exhaled breath according to the disclosure includes spectroscopically detecting the narcotic contained in the exhaled breath of a test subject by infrared spectroscopy using a dispersive grating spectrometer.

An example of a method for sensing a narcotic in an exhaled breath according to the disclosure includes using an infrared spectroscopic technique configured to detect trace gas or trace particles of cannabinoids, opioids, or terpenes contained in the exhaled breath of a test subject based on a unique spectral absorption characteristic associated with each of the cannabinoids, opioids or terpenes.

Items and/or techniques described herein may provide one or more of the following capabilities, as well as other capabilities not mentioned. A breath sample may be received from a test subject. The breath sample may be obtained via a detachable breath sampler device including a filter material or with a handheld breathalyzer with a filter material. The filter material may be placed between a tunable laser source and a photodetector. The intensity of the infrared light may be measured by the photodetector. One or more spectral absorption lines associated with a narcotic such as THC and opioids may be identified. The concentration of narcotic may be determined based on the spectral absorption line. Absorption data and concentration values may be output to a display or other networked devices. Other capabilities may be provided and not every implementation according to the disclosure must provide any, let alone all, of the capabilities discussed. Further, it may be possible for an effect noted above to be achieved by means other than that noted, and a noted item/technique may not necessarily yield the noted effect.

DETAILED DESCRIPTION

Figure 1:
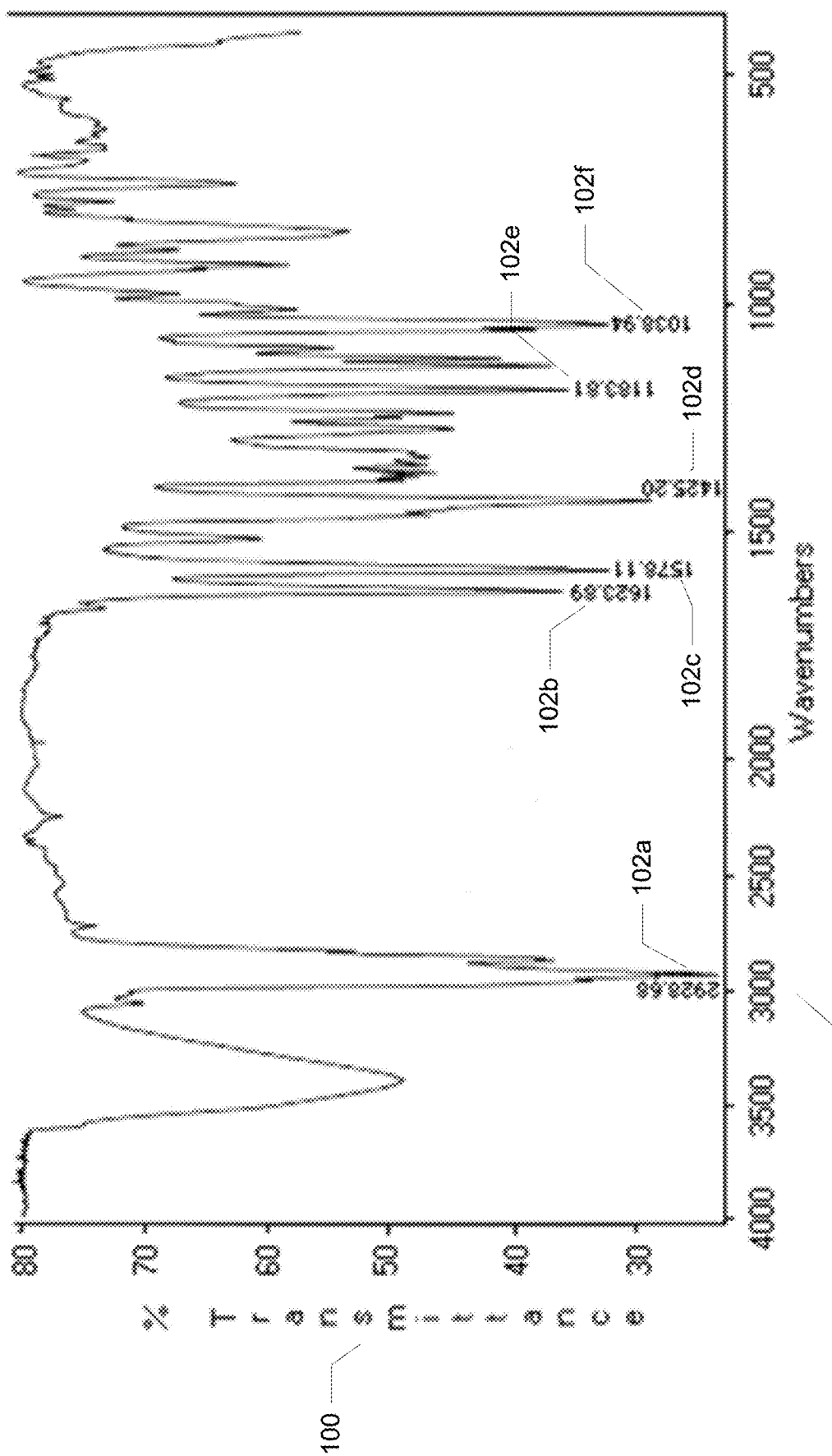
FIG. 1 is an example plot of an infrared spectral transmission of THC power on an infrared-transparent KBr plate.

Techniques are discussed herein for measuring the amount of tetrahydrocannabinol (THC) or opioids contained in the exhaled breath of an individual who recently ingested (e.g. smoked, injected, consumed) marijuana or other narcotics (e.g., opioids), and who is suspected of being intoxicated. As marijuana is gradually being legalized and opioid abuse in increasing, there is increasing concern that the widespread use of such substances will lead to increased automobile and other transportation related accident rates. There is great interest in being able to measure the degree of intoxication of vehicle operators and other personnel whose partial impairment could result safety hazards. Standard methods for quantitative determination of THC contained in samples of blood or urine consist of high-pressure liquid chromatography (HPLC) and gas chromatography-mass spectroscopy (GC-MS). Both of these methods are quantitative but cumbersome and expensive, requiring complex equipment that occupies a large volume, and is mostly confined to analytical laboratories. Detecting opioids generally rely on blood and urine tests. The techniques provided herein utilize infrared spectroscopy to quantitatively measure the THC and/or opioid content in the exhaled breath of individuals suspected of being intoxicated. A new generation of human intoxication measurement instruments may be used to create a positive impact on reducing intoxication-related accidents and assist in identifying opioid abuse. These techniques are examples only, and not exhaustive.

The high lipid solubility of cannabinoids results in their persisting in the body for long periods of time. Even after a single administration of THC, detectable levels of THC can be found in the body for weeks or longer. A number of investigators have suggested that this is an important factor in marijuana's effects. There are three accepted laboratory methods for detecting THC in individuals that have smoked or ingested marijuana: (1) urine testing, for which passive inhalation up to 22 minutes for infrequent users can be detected for 7-10 days after inhalation, with longer periods for heavy users, (2) hair testing, with THC being detectible for up to 90 days after inhalation, and (3) blood and oral fluid testing, for which THC can be detected for 2-24 hours after use in most cases, but for up to 2 weeks in some heavy users. A detailed investigation of the relationship between time after marijuana smoking and relative subject impairment provides an estimate of the relative degree of impairment (defined under Standardized Field Sobriety Tests) as a function of time after smoking various smoke concentrations of THC is shown in Table 1.

TABLE 1

Relationship between time after smoking, blood THC concentration (ng/mL) and percent of impaired subjects by Standardized Field Sobriety Tests

| Dose | Time 1 (0-5 mins) | | Time 2 (50-55 mins) | | Time 3 (100-105 mins) | |
|---|---|---|---|---|---|---|
| | Blood THC | % impaired | Blood THC | % impaired | Blood THC | % impaired |
| Placebo | 0 | 2.5 | 0 | 7.5 | 0 | 5 |
| 1.74% THC | 55.5 | 23 | 6.8 | 23 | 3.7 | 15 |
| 2.93% THC | 70.6 | 46 | 6.2 | 41 | 3.2 | 28 |

From Table 1 it can be seen that the peak blood content of THC concentrations occur within a few minutes after smoking, the blood content of THC decreases to ~10% of its initial value about an hour after smoking cessation, while the relative degree of impairment decreases to only about half of its initial value. Urine THC concentrations of 50 ng/mL are typically considered as the cutoff value for marijuana screening under federal workplace drug testing, although many marijuana smokers exhibit post-smoking urine THC concentrations below that. Taking into consideration the fact that blood THC concentrations decrease to only 10% of the peak value an hour after smoking, a lower THC screening threshold of ~20 ng/mL can be used.

Numerous studies have attempted to determine the preferred THC dose of marijuana users, and a dose of ~300 μg of THC/kg body weight, corresponding to ~21 mg THC in a 70 kg (154 lb) individual, appears as a good estimate. The peak effects of THC occur after the blood concentration has peaked and begun to decline, so typical marijuana smokers with blood THC concentrations of 1.5 ng/mL within 6-8 hours of smoking would exhibit impairment of some psychomotor functions shortly after smoking. These observations suggest that there should be concern over driver impairment with blood THC concentrations greater than ~2 ng/mL.

None of the above-noted, standard laboratory methods of testing THC concentrations in marijuana smokers is suitable for rapid measurement on suspected intoxicated drivers when taken off the road by law enforcement personnel. Any sampling and subsequent chemical analysis of hair, blood, urine or other body fluids of suspected intoxicated drivers by HPLC or GC-MS is time consuming, expensive, impractical, and could involve legal issues related to civil liberties.

Recently there has been an attempt to introduce a new, non-invasive method of measuring the THC content in the exhaled breath of marijuana smokers by sampling the exhaled breath and using High-Filed Asymmetric Waveform Ion Mobility Spectrometry (FAIMS). Three companies (Cannabix, Breathtec Biomedical and Owlstone) are currently commercializing this technology. This measurement technique is somewhat related to MS but does not require a magnetic field or a vacuum environment for its operation. FAIMS has been used to measure a variety of volatile organic compounds (VOCs) as contained in the exhaled breath of individuals. FAIMS is based on the fact that when a ion, surrounded by a non-vacuum buffer gas, experiences an applied electric field, it will drift at a terminal velocity that is related to the field strength, very much like the electrons in a semiconductor are known to drift at a velocity (drift velocity) determined by its interaction with the semiconductor crystal lattice vibrations (phonons). The VOCs are ionized by application of a high electric field, of the order of 10 kV/cm. The ion cross-sections will determine their electric field-driven terminal velocity which, in turn, is dependent on the magnitude of the electric field. Thus, the ions are identified by their mobility. The actual mobility measurement is achieved by application of a pulsed electric field that is perpendicular to the accelerating electric field. The VOC vapor is first ionized and then passed between two parallel plates upon which an alternating voltage is applied across the plates, creating an alternating electric field between the plates. This electric field is applied in a direction perpendicular to the initial direction of the ion. Thus, the ions travel in a saw-tooth trajectory. Each ion-type is characterized by its own unique chemical fingerprint. Whereas FAIMS is potentially an inexpensive method of detecting THC in exhaled breath, results reported to date are not accurate enough to produce legally convincing measurements.

The presence of opioids in the exhaled breath of opioid users may also be detected by analyzing the composition of the aerosols contained in exhaled breath by means of infrared spectroscopic technique. The opioid molecules carried in the bloodstream enter the lung via the pulmonary arteries which carry the deoxygenated blood from the right ventricle to the lungs. The blood then passes through capillaries adjacent to alveoli of the lungs, becoming oxygenated in the process of respiration. The lungs are estimated to have between 300 million and 500 million alveoli, presenting a very large area over which both oxygen is absorbed through the alveoli and over which aerosols (including opioids) are transferred from the blood into the exhaled breath. Exhaled aerosols have been investigated for lung disease diagnostics wherein the aerosols are collected in filter membranes much like the aerosol collection method planned for the proposed work described here. Much like aerosols, infectious viruses of sizes ranging up to ~0.4 μm have also been found to be contained in exhaled breath. The exhaled breath of opioid users contains trace quantities of opioid aerosols which can be trapped in polymer filters whose pore sizes are in the range of 0.2 to 0.5 μm. As described herein, infrared spectroscopy may be used to detect and quantify the presence of opioids based on their unique infrared absorption signatures.

Referring to FIG. 1, plot of an infrared spectral transmission of THC power on an infrared-transparent KBr plate is shown. The plot includes a transmittance axis 100 to indicate percent transmittance, and a wavenumber axis 101. The plot also indicates a number of absorption lines 102*a-f* Infrared spectroscopy is based on measurement of the optical spectral features that are unique to each molecular species. Large organic molecules such as THC are known to have unique optical absorption spectral features in the mid-IR spectral region. The most widely used instruments for carrying out infrared spectroscopy are dispersive (i.e., a dispersive grating spectrometer) and interferometric Fourier Transform InfraRed (FTIR). A much more sensitive method of measuring trace amounts of organic molecular species is based on tunable laser spectroscopy (TLS), where a spectrally-narrow light source (i.e., a laser) is frequency-tuned through a specific, unique spectral region of the molecular species being detected. Such TLS has been shown to be capable of detecting trace gas concentrations in the parts-per-billion (ppb) range. For example, it has been shown that in powder form THC has a distinctive infrared optical transmission spectrum that exhibits strong, sharp absorption lines 102*a-f* in the infrared spectral region, as shown in FIG. 1.

The sharp spectral absorption lines 102*a-f* are unique to THC and therefor provide a tool for quantitatively measuring the THC concentration in the exhaled breath of marijuana smokers. The exhaled breath of marijuana smokers contains relatively high concentrations of THC as well as much lower concentrations of numerous other narcotics and related cannabinoid molecules, which may be characterized by unique spectral absorption signatures in the mid-infrared optical spectral region. As used herein, the term narcotic generally refers to drugs (such as opium or morphine) that in moderate doses dulls the senses, relieves pain, and induces profound sleep but in excessive doses causes stupor, coma, or convulsions, as well as drugs (such as marijuana or LSD) subject to restriction similar to that of addictive narcotics whether physiologically (see physiological) addictive and narcotic or not. Large organic molecules such as those associated with the common opioids are characterized by infrared absorption bands in the 1600-700 cm-1 photon energy region, corresponding to the 6.25-14.3 µm mid-infrared (MIR) wavelength region, respectively, as well as in the 3600-2700 cm-1 photon energy region, corresponding to the 2.8-3.7 µm MIR wavelength region, respectively. For example, oxycodone displays narrow spectral lines at approximately 3000 $cm^{-1}$ and 700-1500 $cm^{-1}$, fentanyl displays strong absorption lines 1580-1680 $cm^{-1}$, and morphine displays broad absorption 3000 $cm^{-1}$ and narrow absorption lines at 600-1130 $cm^{-1}$. It is possible to rapidly, reliably and practically measure the THC and opioid content in the exhaled breath of suspected users by infrared spectroscopy, and that this can in turn be related to the degree of subject intoxication. Examples of the optical spectroscopy techniques capable of carrying out such measurements include FTIR and TLS.

An FTIR interferometer may have sensitivity advantages over a conventional dispersive monochromator-type spectrometer. For example, in the latter there is typically a tradeoff between spectral resolution and sensitivity (e.g., narrower entrance/exit slits result in increased spectral resolution but decreased optical power throughput), whereas the FTIR interferometer does not have that tradeoff. FTIR interferometers may almost instantaneously present the sample absorption spectrum over the entire spectral range (typically 500-4000 cm-1) with improved (e.g., 1-2 cm-1) spectral resolution. In an example, an alternative TLS ultra-high-resolution infrared spectroscopy system utilizing TLS such as grating-tunable quantum cascade lasers (QCLs) may inherently be more sensitive but may also be more expensive and may be limited in spectral range.

In general, large organic molecules exhibit complex molecular resonances corresponding to the vibrational and rotational motion of the atoms comprising the molecules, typically occurring at energy values in the 500-4000 $cm^{-1}$ range, corresponding to infrared wavelengths ranging from 20-2.5 µm, respectively. FTIR interferometry is widely used for identification of organic molecular species. The operating principle is based on the transmission of a spectrally broad light source through an interferometer and onto a sample whose spectral transmission is to be measured. In the FTIR instrument the light is passed through a beamsplitter which sends the light in two orthogonal directions. One beam goes to a stationary mirror then back to the beamsplitter. The other goes to a mirror moving at a constant velocity normal to the mirror. The constant-velocity motion of the mirror results in a total light path length that is variable compared to the fixed stationary mirror light beam path length. When the two light beams meet at the beam splitter they recombine, but the difference in light path lengths creates constructive and destructive interference as a function of time, resulting in a frequency domain interferogram. The recombined beam passes through the sample to be analyzed. The sample absorbs certain wavelengths which are therefore subtracted from the interferogram. The detector records variation in energy vs time for all wavelengths simultaneously. Mathematically there is a reciprocal relationship between time domain and frequency domain functions. The Fourier transform enables conversion of the light intensity vs. time spectrum into a light intensity vs. light frequency (units of $cm^{-1}$) spectrum. Thus the FTIR interferometer provides a graph of the spectrally broad light transmitted through the sample as a function of photon energy (e.g., light energy in units of $cm^{-1}$). This analytical tool may be used to characterize the infrared absorption characteristics of opioids and THC including related cannabinoid molecules.

Figure 2:
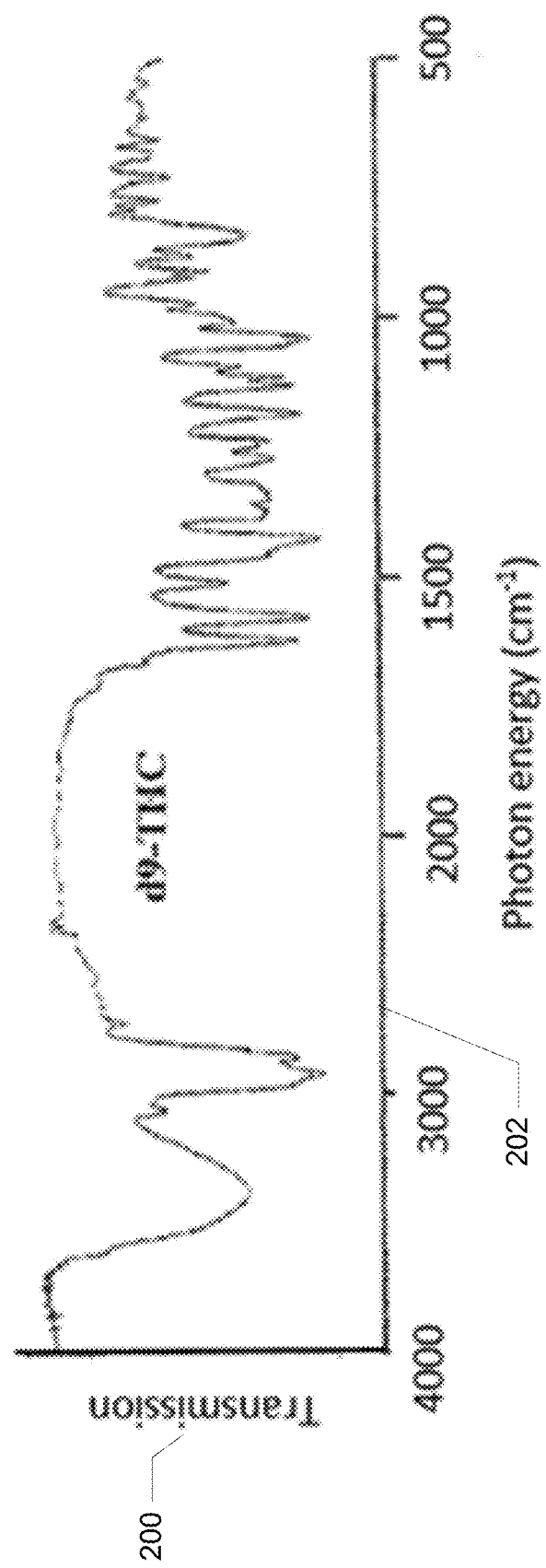
FIG. 2 is an example plot of infrared spectral transmission of THC dissolved in ethanol.

Referring to FIG. 2, an example plot of infrared spectral transmission of THC dissolved in ethanol is shown. The plot includes a transmission axis 200 and a photon energy axis 202. FIG. 2 shows the measured transmittance of infrared light through a liquid (ethanol) sample cell containing dissolved THC. As is the case for THC powder, there is significant spectral fine structure in the 600-1700 $cm^{-1}$ region. This spectral absorption signature is unique to THC, being determined by the specific structure of the THC molecule. Related cannabinoids have similar absorption behavior because their chemical structures are similar, but their concentration in exhaled smoker breath is significantly less than that of THC. There is concern that the other exhaled breath gases passing through a gas absorption cell (such as $H_2O$, $N_2$, $CO_2$, etc.) could have spectral absorption lines that occur in the same spectral region as those of THC and thereby confound measurements. It is therefore important to identify the optimal spectral region for THC absorption with minimal interference from confounding gases.

Figure 3:
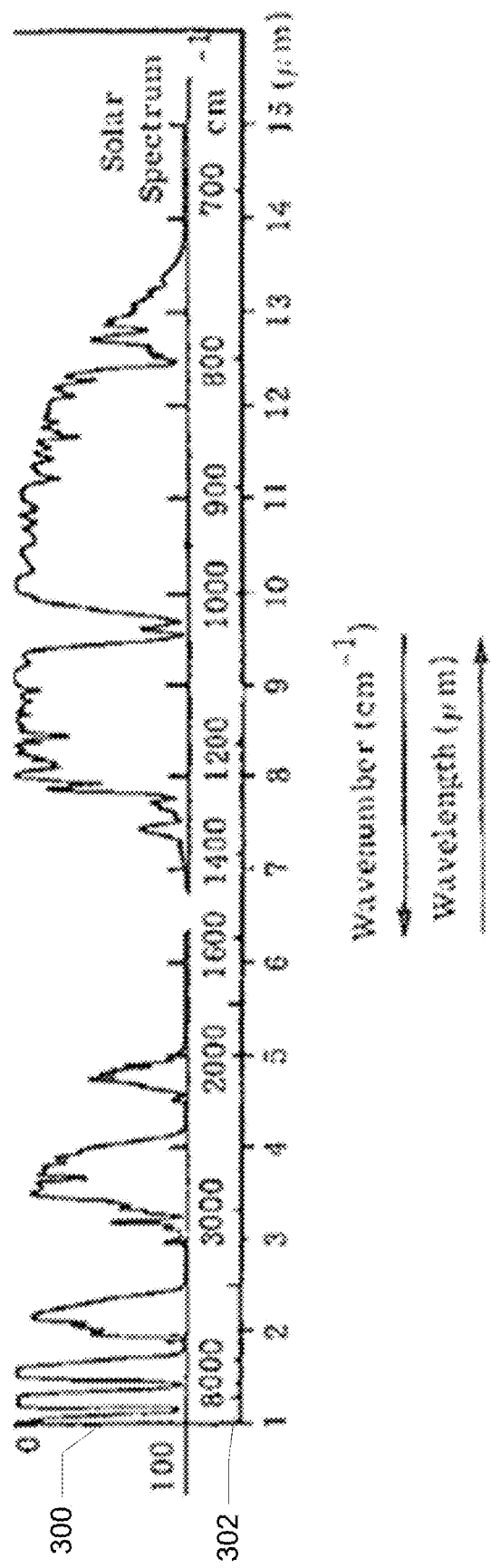
FIG. 3 is an example plot of the spectral transmission of the atmosphere over a 0.3 km path length.

Referring to FIG. 3, an example plot of the spectral transmission of the atmosphere over a 0.3 km path length is shown. The plot includes a transmission axis 300 and a wavenumber/wavelength axis 302. As depicted, atmospheric gases do not have significant spectral absorption in the region of interest for THC sensing. The atmospheric absorption in much of the mid-IR spectral region is low (i.e., high transmission). Since exhaled breath, while known to contain trace amounts of thousands of different organic chemicals, is basically similar to that of the atmosphere, this spectral region is convenient for spectrally analyzing exhaled breath for the presence of THC. Specifically, referring to FIG. 1, it can be seen that THC has a strong and relatively narrow spectral absorption line 102f at 1036.94 cm$^{-1}$ (~9.64 μm) where there are no competing absorption lines from any atmospheric gases. There is additional, well-defined spectral absorption structure in the nearby spectral regions. Furthermore, the related cannabinoids, less numerous than THC ($C_{21}H_{30}O_2$), such as Cannabinol ($C_{21}H_{26}O_2$), Cannabigerol ($C_{21}H_{32}O_2$), and Cannabicyclol ($C_{21}H_{30}O_2$), also have spectral absorption characteristics that are very similar to those of THC, although their abundance may be significantly lower. The compound Cannabidiol ($C_{21}H_{30}O_2$), also known as CBD, while having the same atomic composition as THC, differs from THC in its molecular structure, making it possible to distinguish between THC and CBD by infrared spectroscopy. This may be an important issue because, whereas THC is known to cause euphoria, CBD does not cause euphoria and has been shown to have medical therapeutic value.

There is potentially confounding infrared spectral absorption in the 9.5-10 μm spectral region arising from an estimated 4000 identified trace chemicals, some of which (e.g., carbon monoxide, benzene, ammonia, formaldehyde and hydrogen cyanide) are formed during combustion of the tobacco. Most of the marijuana smoke ingredients consist of a broad range of polycyclic aromatic hydrocarbons (PAHs) whose presence is known to be much lower than that of THC and the related cannabinoids. This fact combined with the absence of significant spectral absorption by atmospheric gases in the 9.5-10 μm spectral region around the strong 9.64 μm THC spectral absorption band indicates that this spectral region may be used for spectroscopic investigation of the exhaled breath of marijuana smokers. Other spectral regions associated with other narcotics may also be used.

Figure 4:
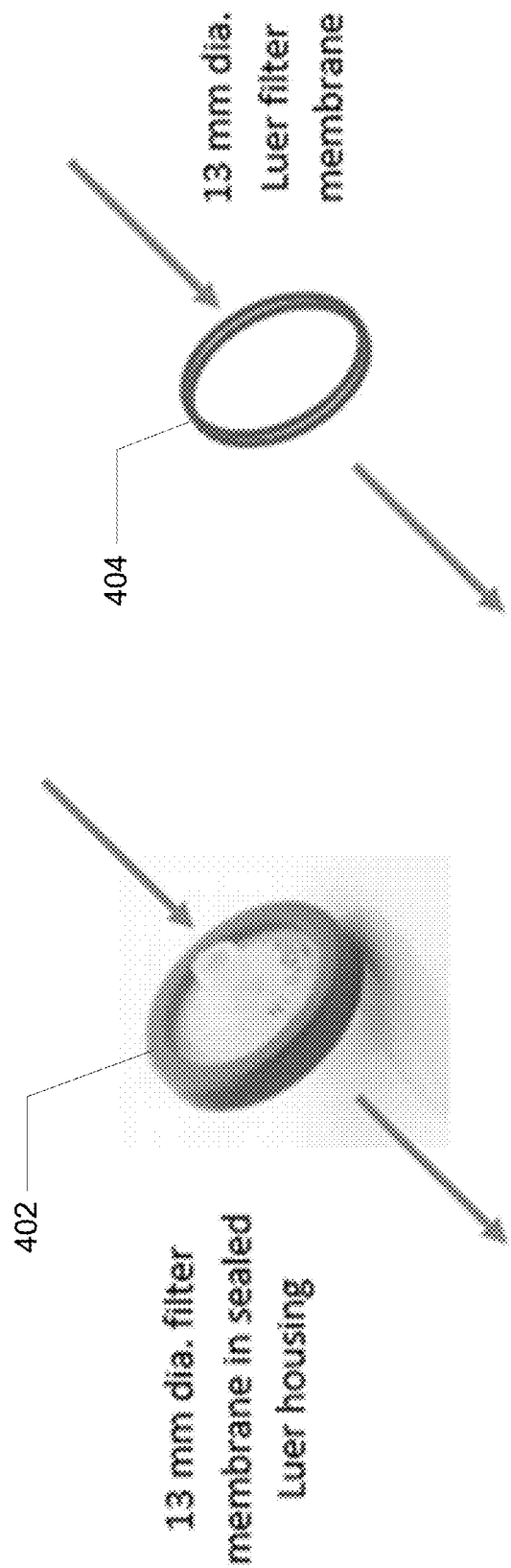
FIG. 4 are example filters for capturing THC aerosols in an exhaled breath.

Referring to FIG. 4, example filters for capturing THC aerosols and opioid aerosols in an exhaled breath are shown. The example filters include a Luer filter sealed in an enclosure 402 and a Luer filter membrane 404. The Luer filters are examples only and not limitations as a variety of THC or opioids in exhaled breath measurement configurations may be used. The Luer filters provide a convenient and relatively inexpensive option. The Luer filter membrane 404 may be either contained in a sealed Luer enclosure 402 or it may be inserted into a Luer filter cartridge (not shown in FIG. 4). In either case, the exhaled breath is introduced into the filter cartridge wherein the filter captures the THC and/or opioid aerosols. As an example, Luer filters are typically available in a variety of diameters (e.g., 5, 10, 13, 15 mm diameter). Measurement of the THC and opioid concentration may then be carried out in either an FTIR interferometer or in a tunable laser spectroscopy system using a commercially-available, frequency-tunable laser, such as a quantum cascade laser (QCL) operating at room temperature. In operation, an interrogation light beam passes through the Luer filter onto a photodetector. The Luer filter membrane is typically a polymer such as PTFE, PVDF, polyethylene (PE) or similar polymer whose infrared absorption characteristics are known. For the case in which the sealed Luer filter is used, the filter housing, also being produced from polymer material, has known infrared absorption characteristics. The THC and other opioid absorption line frequencies may be selected so as not to coincide with any of the polymer material absorption regions, the latter of which can be measured in an empty filter cartridge.

Figure 5:
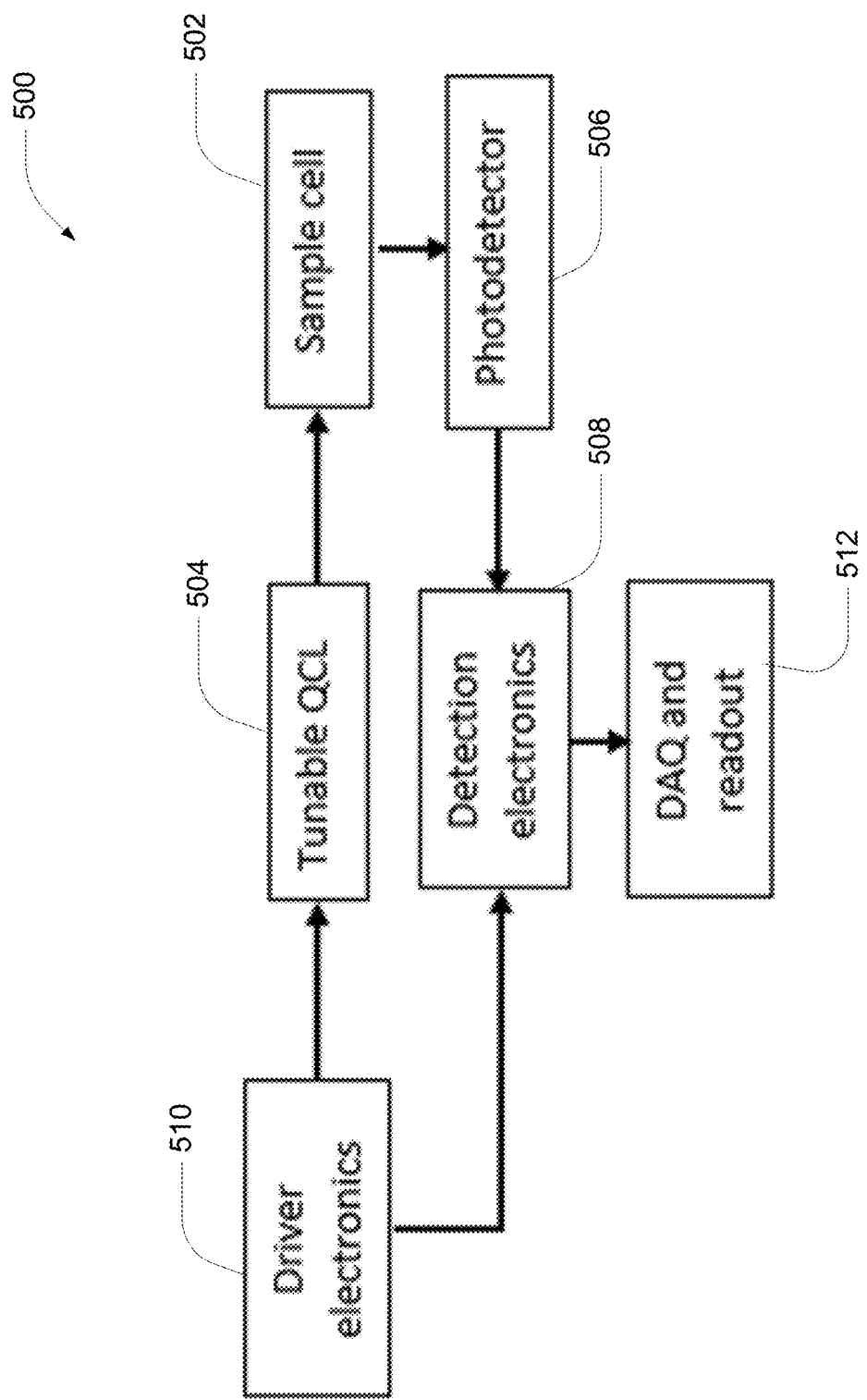
FIG. 5 is a schematic illustration of an example Quantum Cascade Laser (QCL) tunable laser spectroscopy (TLS) technique.

Referring to FIG. 5, a schematic illustration of an example Quantum Cascade Laser (QCL) tunable laser spectroscopy (TLS) technique 500 is shown. The technique 500 includes a sample cell 502 (e.g., configured to hold a filter material), a tunable QCL 504, at least one photodetector 506, detection electronics 508, driver electronics 510 and a data acquisition (DAQ) and readout module 512. The most sensitive photodetectors for this application are either photon detectors such as HgCdTe or photoacoustic detectors such as resonant acoustic cells equipped with a sensitive microphone or MEMs-based optical microphone coupled with a laser readout interferometer (e.g., see L. Sholtz and S. Palzer, Photoacoustic-based detector for infrared laser spectroscopy, Applied Physics Letters 109, 041102 (2016)). The QCL-based spectroscopy technique 500 provides high sensitivity (e.g., into a part-per-billion range), and may be assembled within a small form factor instrument configuration because of the relatively small sizes of QCL devices. For example, the technique 500 may be implemented on a computerized device with at least one processor and driver electronics 510 that provide a control signal (e.g., electrical current) to activate the QCL 504 and simultaneously provide a reference signal to the detection electronics 508. Such driver electronics typically consist of one or more commercially available operational amplifiers and related circuitry designed to drive an electrical current through the QCL whose light output power is then a function of the driver current. Other control systems and control signals may be used to control a laser output. The QCL 504, whose coarse emission wavelength is pre-selected by a grating, is fine-controlled by the amplitude of the drive current and is transmitted through the sample cell 502 which consists of a polymer (or other IR transparent, porous material) onto a photodetector 506 such as a commercially-available, thermoelectrically cooled HgCdTe photoconductor. The QCL 504 may be a tunable laser source such as a diode laser, a solid-state laser, a gas laser, other type of laser whose output optical frequency can be electronically or mechanically controlled. The electrical output signal from the photodetector is fed into the detection electronics 508, where it can be synchronized with the reference input signal emanating from the driver electronics 510. The resulting output signal which contains the THC spectral information of interest is then fed into data acquisition (DAQ) electronics configured so as to provide user-friendly readout information in the form of a graph of transmitted optical signal intensity vs. QCL emission frequency (in cm$^{-1}$, for example). Such measured data can then be compared to stored THC absorption data and, by use of appropriate algorithms, the absolute THC concentration (e.g., in pg/mL of exhaled breath) can be determined and displayed on a PC, laptop, tablet or other display device. As examples, and not a limitation, QCL-based spectroscopic systems of this type are commercially available from such as Daylight Solutions, Pranalytica, and Bloch Engineering. Other entities also provide components in the market.

An alternative method for measuring the infrared absorption characteristics of narcotics such as cannabinoids, opioids or other lung-exhaled chemicals involves the use of optical frequency comb laser. An optical frequency comb is a laser source whose spectrum consists of a series of discrete, equally and closely spaced optical frequency lines. Such a frequency comb can be obtained by pulsing a laser periodically in time with very short duration pulses at high repetition rates, such as can be achieved by mode locking or by external pulse excitation. Frequency comb based infrared spectroscopy systems using QCLs are currently available from IRsweep (Stafa, Switzerland), and it is anticipated that other manufacturers of such systems may soon enter the field.

TLS is inherently much more sensitive than FTIR spectroscopy for two fundamental reasons: (1) the spectral brightness of a tunable QCL source is several orders of magnitude greater than that of a thermal source (basically a black-body such as a globar for example) because all of the emitted light energy in a laser beam is contained in a spectrally-narrow spectral region whereas the light energy in a thermal (globar) light source is spread over a very wide spectral region, and (2) the sensitivity of the photodetector (whether a photon detector or a photoacoustic detector) in a typical TLS system is several orders of magnitude higher than that of the spectrally broad thermal photodetectors used in FTIR system.

In operation, the tunable QCL 504 may be electronically frequency tuned (e.g., by tuning the laser drive current with the driver electronics 510 which, in turn changes the QCL chip temperature which changes the material refractive index and thereby changes the optical emission frequency, or, more typically tuning the QCL by use of an external grating whose rotation changes the wavelength at which the laser emits, such as is found in tunable QCL spectroscopy systems produced by Daylight Solutions, Pranalytica and Block Engineering.) The photodetector 506 may be configured to detect the intensity of the tunable IR light that traverses the sample cell 502, and the photodetector signal is then amplified and synchronized with the driver frequency in the detection electronics 508. Following data acquisition (DAQ) in the DAQ module 512 the absolute spectral absorption may be displayed in the readout module on a built-in display or external monitor such as via a connected laptop PC or tablet. Other electronic detection methods may be used, including derivative methods that may enhance system sensitivity.

In general, the sensitivity of tunable laser detection systems is higher than that of conventional grating dispersion spectrometers. In an embodiment, conventional grating dispersion may be used to detect if large THC or opioid concentrations are known to exist. Typically, however, such large THC or opioid concentrations do not exist in the exhaled breath of users because it has been previously shown that typical marijuana smokers' exhaled breath contains of the order of nanograms of THC when captured over a number of exhaled breath volumes. Such small quantities of THC may not be detectable by conventional grating dispersion spectrometers.

Figure 6A:
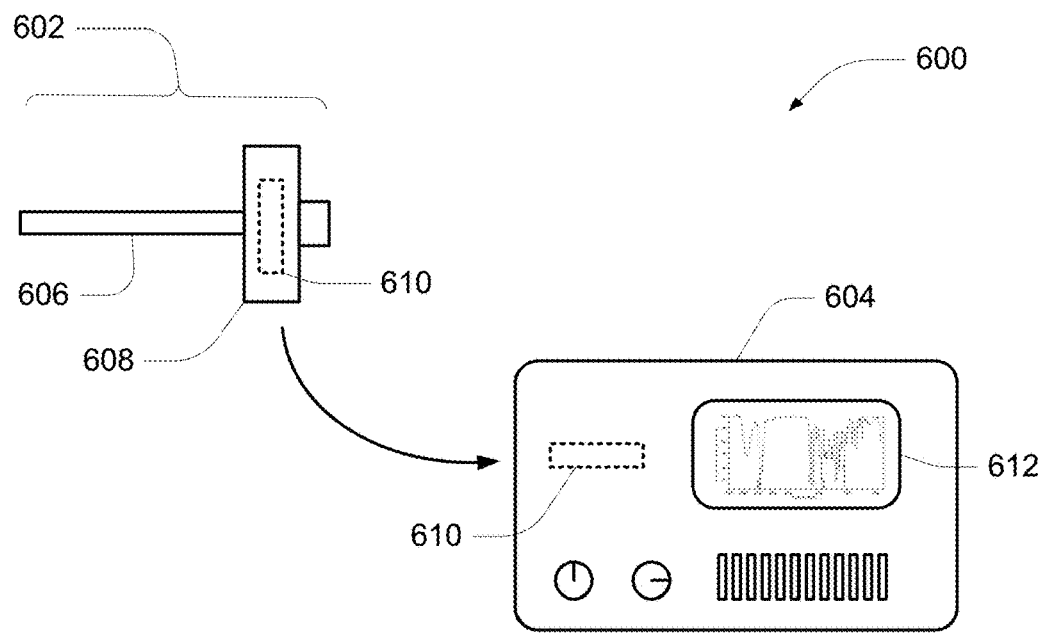
FIGS. 6A and 6B are examples of portable narcotic breathalyzers.
Figure 6B:
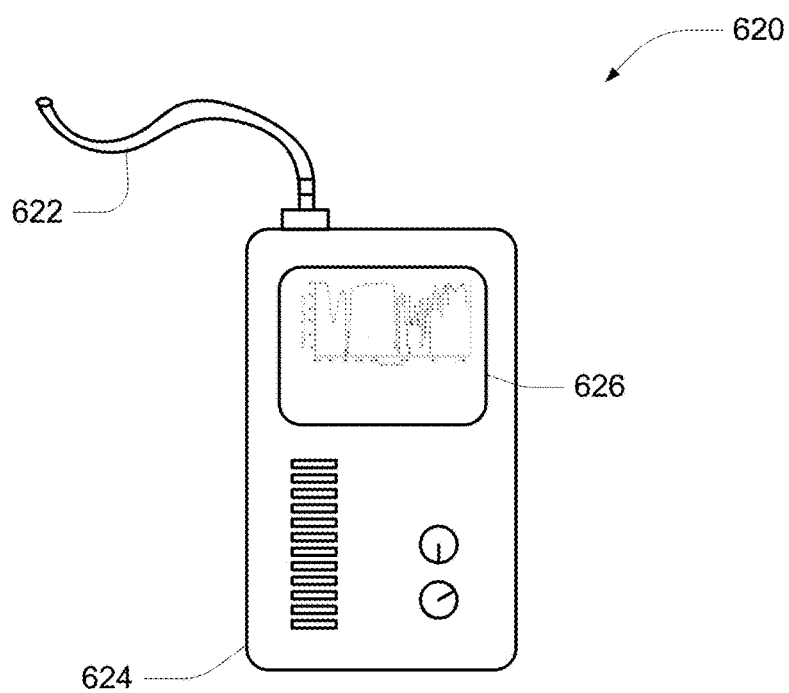

Referring to FIGS. 6A and 6B, examples of portable narcotic breathalyzers are shown. The portable breathalyzers may be implemented on computerized devices. In an example, a two-part breathalyzer 600 includes a breath sampler device 602 and an analyzer device 604. The breath sampler device 602 may include a tube 606 configured to receive the exhaled breath of a test subject and a filter holder assembly 608 configured to hold a filter 610 in the path of the exhaled breath. The filter 610 may include filter material. In an example the filter material may be a gas filter material, a liquid filter material, a solid filter material, or other such filter material. In an example, the filter 610 is a Luer filter membrane 404. After the test subject exhales in to tube 606 (e.g., based on a number of exhaled breaths, an amount of time, etc.), the filter 610 may be placed into the analyzer device 604. The analyzer device 604 may include the elements of the QCL tunable laser described in FIG. 5. The results of the analysis (e.g., the DAQ and readout 512) may be presented to a user via a display screen 612. In an example, the analyzer device 604 may be a desktop unit or sized to remain in a vehicle (e.g., police cruiser) for field operations. In an embodiment, a handheld breathalyzer 620 may integrate the breath sampler device 602 and analyzer device 604 into a single form factor. For example, a breathing tube 622 may be operably coupled to a handheld analyzer 624. The handheld analyzer 624 may include one or more sample cells 502 configured to capture particulates (e.g., THC, opioids) in the test subject's breath. The handheld analyzer may include a display 626 to present the results of the data acquisition and output a THC concentration level. In an example, the analyzer device 604 and the handheld analyzer 624 may be configured to exchange data with a network (e.g., IEEE 802.11, BLUETOOTH, LTE, etc.) to enable other devices (e.g., laptop computer, tablet, smartphone, etc.) to obtain and/or display the spectroscopy results.

Figure 7:
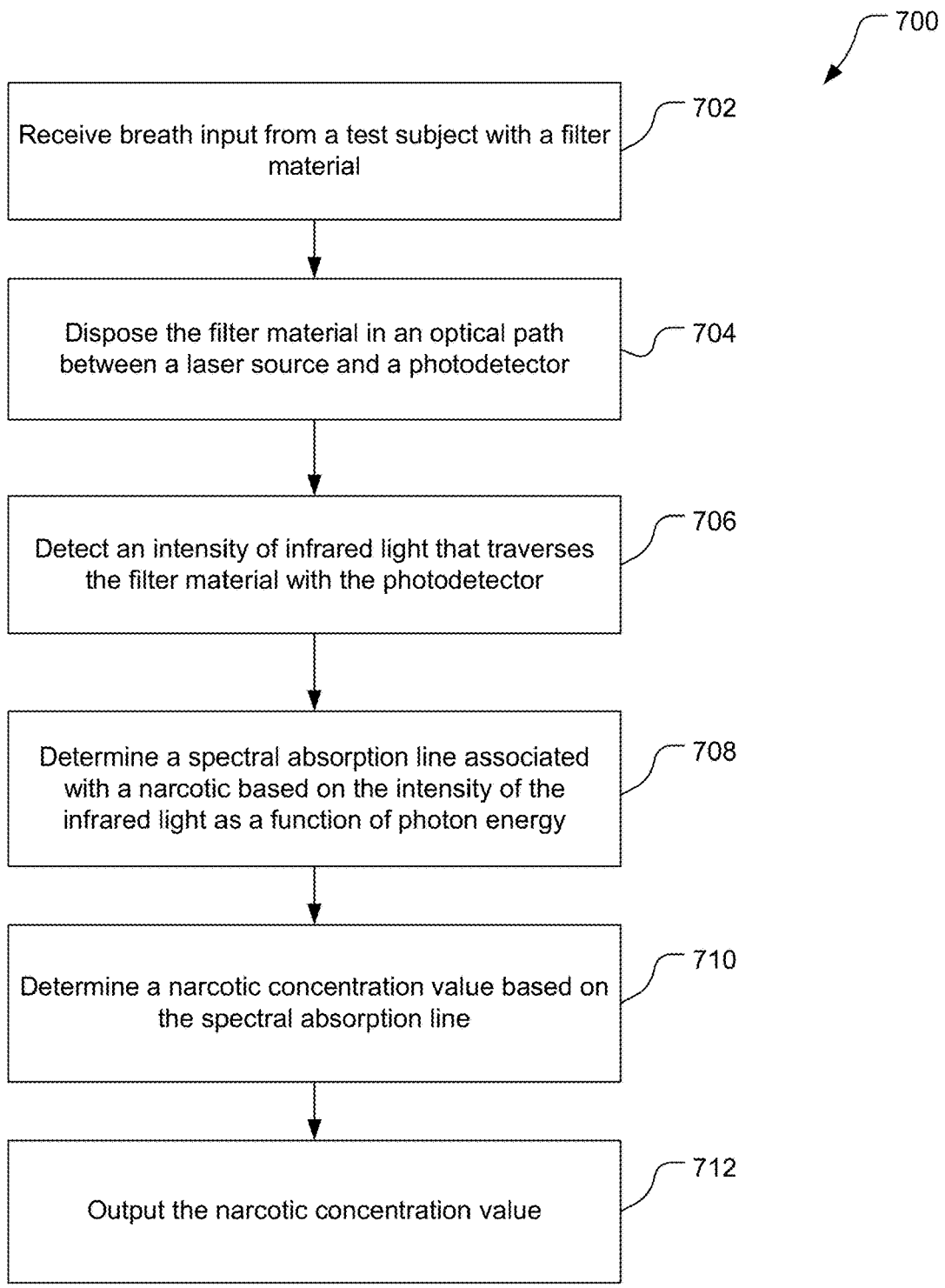
FIG. 7 is an example process flowchart for determining a THC concentration in a breath sample.

Referring to FIG. 7, with further reference to FIGS. 1-6, a method 700 of determining a narcotic concentration in a breath sample is shown. The method 700 is, however, an example only and not limiting. The method 700 may be altered, e.g., by having stages added, removed, rearranged, combined, performed concurrently, and/or having single stages split into multiple stages.

At stage 702, the method includes receiving breath input from a test subject with a filter material. The filter material may be a membrane or other material configured to capture THC and opioid aerosols in an exhaled breath. For example, the filter material may be a gas filter material, liquid filter material, a solid filter material, other such material. In an example, the filter material is the Luer filter membrane 404. In a traffic stop scenario, the test subject may be a vehicle operator which law enforcement believes may be under the influence of a narcotic. A law enforcement official may provide the test subject with a breath sampler device 602 containing the filter material and instruct the test subject to blow (e.g., exhale) into the tube 606. The breath sampler device 602, including the filter 610, may then be placed into the analyzer device 604 located within a law enforcement vehicle. In an example, the filter 610 may be removed from the breath sampler device 602 and placed within the analyzer device 604. In an embodiment, the breath input may be received via the breathing tube 622 coupled to the handheld breathalyzer 620.

At stage 704, the method includes disposing the filter material in an optical path between a laser source and a photodetector. Referring to FIG. 5, the filter material is a sample cell 502 located between the tunable QCL 504 and the photodetector 506. The filter material may be a Luer filter membrane 404 moved from the breath sampler device 602 into the analyzer device 604. In an example, the filter material may be disposed between tunable QCL or an optical frequency comb laser 504 and the photodetector 506 prior to receiving the breath input.

At stage 706, the method includes detecting an intensity of infrared light that traverses the filter material with the photodetector. In an example, the computer systems within the analyzer device 604 are the handheld breathalyzer 620 may be configured to electronically frequency tune the tunable QCL or optical frequency comb laser 504 located therein. The computer system may be configured to modify the laser drive current (e.g., with the driver electronics 510) which will change the QCL chip temperature and the corresponding refractive index/optical emission frequency. The computer system may be operably coupled to the photodetector 506 and configured to detect the intensity of the tunable IR light that traverses the filter material (i.e., the sample cell 502). The computer system may also be configured to amplify and synchronize the photodetector signal with the driver frequency in the detection electronics 508.

At stage 708, the method includes determining one or more spectral absorption lines associated with a narcotic based on the intensity of the infrared light as a function of photo energy. A computer system within the analyzer device 604 and/or the handheld breathalyzer 620 may be configured as the DAQ module 512. The DAQ module 512 may be configured to detect one or more particular spectral absorption lines associated with THC and opioids. For example, referring to FIG. 1, the DAQ module 512 may be configured to detect a spectral absorption line 102$f$ approximately 1036.94 cm$^{-1}$ (e.g., +/−50 cm$^{-1}$) which is associated with THC without a nearby competing absorption lines from atmospheric gases. Other defined IR spectral absorption lines may also be associated with the presence of THC and/or opioids in the filter material. For example, large organic molecules such as those associated with the common opioids are characterized by infrared absorption bands in the 1600-700 cm-1 photon energy region, corresponding to the 6.25-14.3 μm mid-infrared (MIR) wavelength region, respectively, as well as in the 3600-2700 cm−1 photon energy region, corresponding to the 2.8-3.7 μm MIR wavelength region, respectively. For example, oxycodone displays narrow spectral lines at approximately 3000 cm$^{-1}$ and 700-1500 cm$^{-1}$, fentanyl displays strong absorption lines 1580-1680 cm$^{-1}$, and morphine displays broad absorption 3000 cm$^{-1}$ and narrow absorption lines at 600-1130 cm$^{-1}$.

At stage 710, the method includes determining a narcotic concentration value based on the spectral absorption line intensity. In general, the stronger the absorption the weaker the photodetector signal. Calibration factors may be used to obtain absolute absorption values. Such calibration can be achieved, for example, by using reference filter membranes containing known THC and opioid concentration as previously determined by depositing known THC and opioid concentrations onto the reference filter membranes. A representative method of obtaining such known THC and opioid concentrations might be to apply a commercially-available, known THC and opioid weight dissolved in methanol or ethanol solution (e.g., such as available from Cerilliant) of 1 mg/mL from which the methanol or ethanol has been evaporated. Lower THC and opioid concentration reference filter membranes may be obtained by diluting the 1 mg/mL solution with measured amounts of methanol and then depositing that diluted solution onto secondary calibration filter membranes and subsequently evaporating the excess methanol. The known amount of THC and opioids on the reference filter membranes may then be used as secondary reference standards. Since the QCL light absorption in the THC or opioid coated filter membrane is directly proportional to the amount of THC or opioid contained on the filter membrane, comparison of photodetector signal intensity with that of calibration reference samples will provide information on the THC or opioid concentration on the sample filter membranes.

At stage 712, the method includes outputting the narcotic concentration value. In an example, the output may be presented on a display 612, 626 or on a peripheral device such as a printer. The output may be provided to a network resource such as a tablet or laptop computer via a communication protocol (e.g., WiFi, BLUETOOTH). In an example, the analyzer device 604 and handheld breathalyzer 620 may be connected to a remote server configured to perform the detection computations associated with determining the narcotic (e.g., THC, opioids) concentration value and then output the value back to the analyzer device 604 or handheld breathalyzer 620 (e.g., remote processing).

Figure 8:
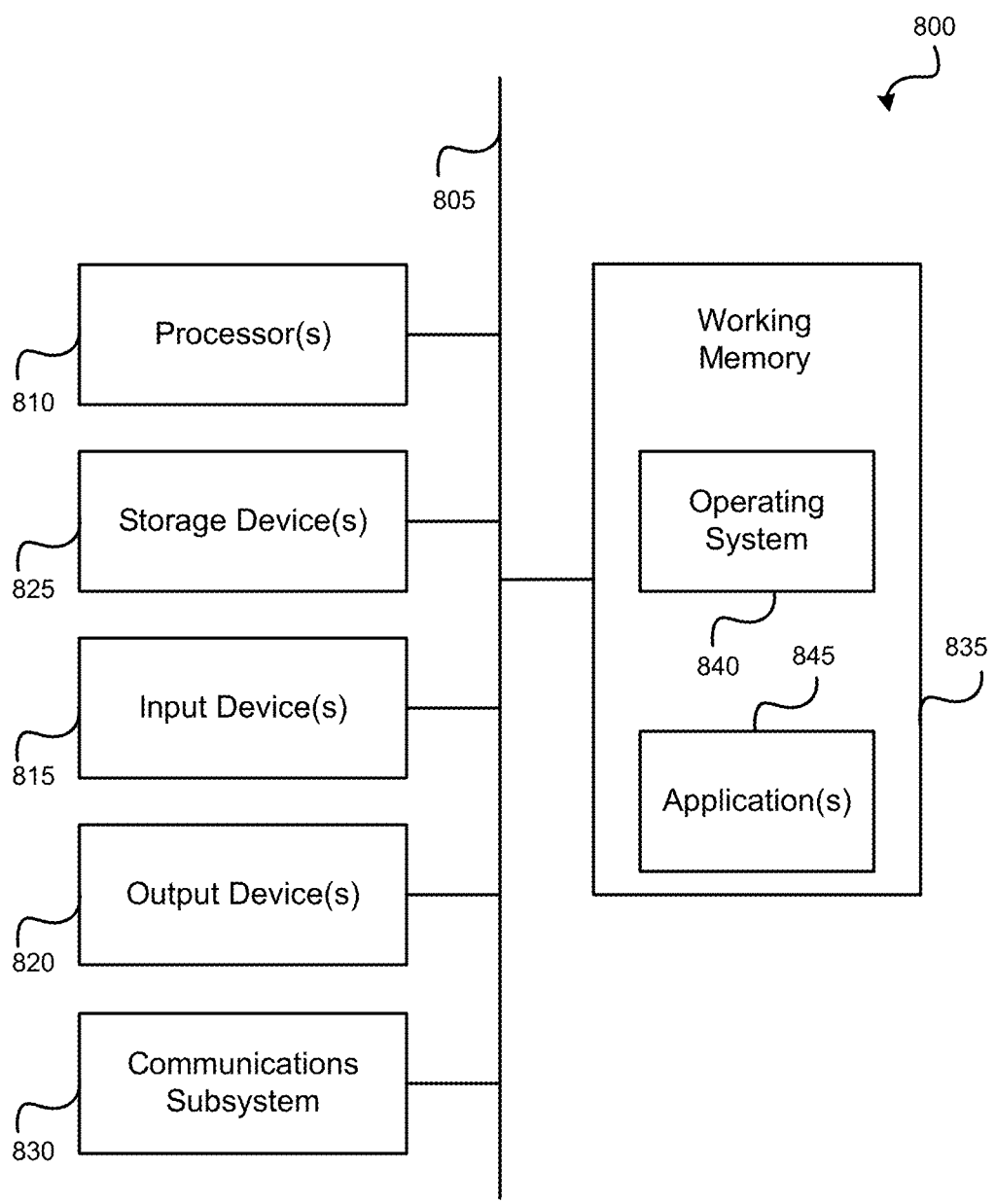
FIG. 8 illustrates a block diagram of an example of a computer system.

Referring to FIG. 8, a computer system as may be incorporated as a computer system within the analyzer device 604, the handheld breathalyzer 620, and/or a remoter server as previously described. FIG. 8 provides a schematic illustration of one embodiment of a computer system 800 that can perform the methods provided by various other embodiments, as described herein. It should be noted that FIG. 8 is meant only to provide a generalized illustration of various components, any or all of which may be utilized as appropriate. FIG. 8, therefore, broadly illustrates how individual system elements may be implemented in a relatively separated or relatively more integrated manner.

The computer system 800 is shown comprising hardware elements that can be electrically coupled via a bus 805 (or may otherwise be in communication, as appropriate). The hardware elements may include at least one processor 810, including without limitation one or more general-purpose processors and/or one or more special-purpose processors (such as digital signal processing chips, graphics acceleration processors, and/or the like); one or more input devices 815, which can include without limitation a touch screen, mouse, a keyboard and/or the like; and one or more output devices 820, which can include without limitation a display device, a printer and/or the like.

The computer system 800 may further include (and/or be in communication with) one or more non-transitory storage devices 825, which can comprise, without limitation, local and/or network accessible storage, and/or can include, without limitation, a disk drive, a drive array, an optical storage device, solid-state storage device such as a random access memory ("RAM") and/or a read-only memory ("ROM"), which can be programmable, flash-updateable and/or the like. Such storage devices may be configured to implement any appropriate data stores, including without limitation, various file systems, database structures, and/or the like.

The computer system 800 might also include a communications subsystem 830, which can include without limitation a modem, a network card (wireless or wired), an infrared communication device, a wireless communication device and/or chipset (such as a BLUETOOTH device, an 802.11 device, a WiFi device, a WiMax device, cellular communication facilities, etc.), and/or the like. The communications subsystem 830 may permit data to be exchanged with a network (such as the network described below, to name one example), other computer systems, and/or any other devices described herein. In many embodiments, the computer system 800 will further comprise a working memory 835, which can include a RAM or ROM device, as described above.

The computer system 800 also can comprise software elements, shown as being currently located within the working memory 835, including an operating system 840, device drivers, executable libraries, and/or other code, such as one or more application programs 845, which may comprise computer programs provided by various embodiments, and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods. For example, the instructions may be configured to enable the processors 810 to perform the functions associated with the driver electronics 510, detection electronics 508 and/or the DAQ and readout 512. The instructions may also be configured to allow the computer system 800 to interact with submodules configured to perform the functions above.

A set of these instructions and/or code might be stored on a computer-readable storage medium, such as the storage device(s) 825 described above. In some cases, the storage medium might be incorporated within a computer system, such as the system 800. In other embodiments, the storage medium might be separate from a computer system (e.g., a removable medium, such as a compact disc), and/or provided in an installation package, such that the storage medium can be used to program, configure and/or adapt a general purpose computer with the instructions/code stored thereon. These instructions might take the form of executable code, which is executable by the computer system 800 and/or might take the form of source and/or installable code, which, upon compilation and/or installation on the computer system 800 (e.g., using any of a variety of generally available compilers, installation programs, compression/decompression utilities, etc.) then takes the form of executable code.

It will be apparent to those skilled in the art that substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer system (such as the computer system 800) to perform methods in accordance with various embodiments of the invention. According to a set of embodiments, some or all of the procedures of such methods are performed by the computer system 800 in response to processor 810 executing one or more sequences of one or more instructions (which might be incorporated into the operating system 840 and/or other code, such as an application program 845) contained in the working memory 835. Such instructions may be read into the working memory 835 from another computer-readable medium, such as one or more of the storage device(s) 825. Merely by way of example, execution of the sequences of instructions contained in the working memory 835 might cause the processor(s) 810 to perform one or more procedures of the methods described herein.

The terms "machine-readable medium" and "computer-readable medium," as used herein, refer to any medium that participates in providing data that causes a machine to operate in a specific fashion. In an embodiment implemented using the computer system 800, various computer-readable media might be involved in providing instructions/code to processor(s) 810 for execution and/or might be used to store and/or carry such instructions/code (e.g., as signals). In many implementations, a computer-readable medium is a physical and/or tangible storage medium. Such a medium may take many forms, including but not limited to, non-volatile media, volatile media, and transmission media. Non-volatile media include, for example, optical and/or magnetic disks, such as the storage device(s) 825. Volatile media include, without limitation, dynamic memory, such as the working memory 835. Transmission media include, without limitation, coaxial cables, copper wire and fiber optics, including the wires that comprise the bus 805, as well as the various components of the communications subsystem 830 (and/or the media by which the communications subsystem 830 provides communication with other devices).

Common forms of physical and/or tangible computer-readable media include, for example, a floppy disk, a flexible disk, hard disk, magnetic tape, or any other magnetic medium, a CD-ROM, any other optical medium, a RAM, a PROM, EPROM, a FLASH-EPROM, any other memory chip or cartridge, a carrier wave as described hereinafter, or any other medium from which a computer can read instructions and/or code.

Various forms of computer-readable media may be involved in carrying one or more sequences of one or more instructions to the processor(s) 810 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 800. These signals, which might be in the form of electromagnetic signals, acoustic signals, optical signals and/or the like, are all examples of carrier waves on which instructions can be encoded, in accordance with various embodiments of the invention.

The communications subsystem 830 (and/or components thereof) generally will receive the signals, and the bus 805 then might carry the signals (and/or the data, instructions, etc. carried by the signals) to the working memory 835, from which the processor(s) 805 retrieves and executes the instructions. The instructions received by the working memory 835 may optionally be stored on a storage device 825 either before or after execution by the processor(s) 810.

Figure 9:
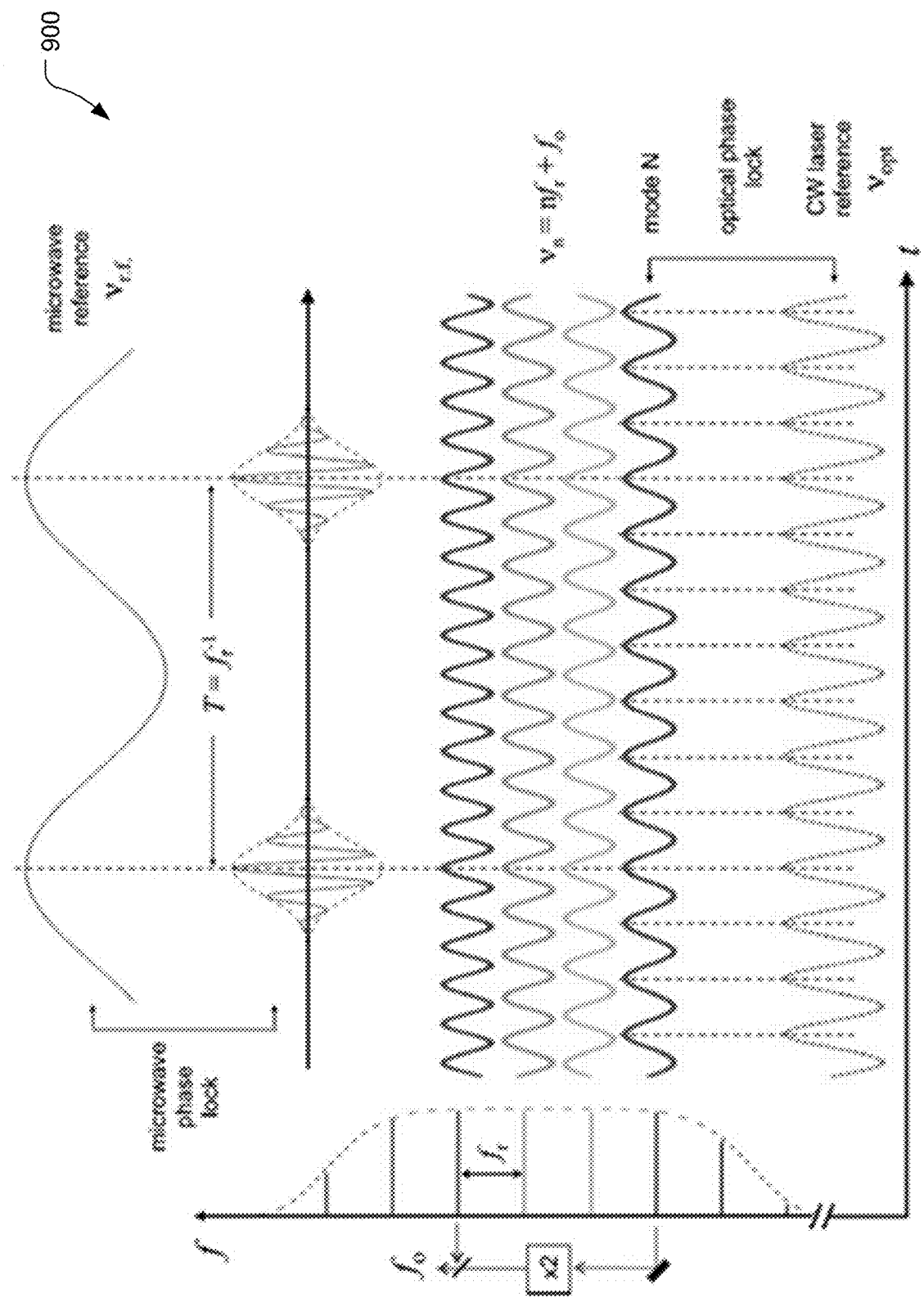
FIG. 9 illustrates the laser frequency comb concept.

Referring FIG. 9, an illustration 900 of a frequency comb concept is shown. The illustration 900 depicts a frequency comb which results from exciting a laser with ultrashort (few femtosecond) electrical pulses at a pulse repetition rate of T (s). The top portion of the illustration 900 represents the laser drive current in the time-domain while the bottom portion of the illustration 900 represents the various laser oscillation modes which, when added result in the top figure laser output waveform. In the frequency domain the bottom figure modes would be represented by a series of equally-spaced impulses, each one representing one of the laser modes. For example, a laser (e.g., a mid-infrared quantum cascade laser) is operated in a mode locked condition so as to generate a series of very short infrared light pulses at, for example, a pulse repetition rate of 100 GHz. In this example, the mode locked laser is operated so as to generate light pulses approximately 120 fs in duration (corresponding to approximately 4 cycles of a 30,000 GHz mid-infrared optical frequency). From the fundamental relation $c=\lambda v$, where c is the velocity of light in space, $\lambda$ is the laser light wavelength, and v is the optical frequency, the 30,000 GHz optical frequency corresponds to a mid-infrared light wavelength of 10 μm, corresponding to a photon energy of 1000 cm-1. This lies in the infrared spectral region where molecular resonances observed in aerosols of THC, CBD, opioids and related exhaled breath condensates occur. The laser excitation mechanism and the resulting pulsed laser waveform described here is depicted in the upper portion of the illustration 900.

Continuing the example above, assuming that the mode locking frequency occurs at 100 GHz, the pulsed (120 fs) laser light output waveform can be visualized as shown in the top portion of the illustration 900. That time-domain laser output waveform (e.g., 120 fs wide pulses separated by 10,000 fs time intervals) can be visualized as being the result of adding the optical signals from the same laser but consisting of many laser modes whose optical frequencies are given by the relation $v_n = nf_r + f_0$, where n is an integer. Four representative time domain waveforms are shown in the middle portion of the illustration 900, labeled mode n (lower), mode n+1, mode n+2, and mode n+3 (upper). In the time domain these 4 modes add constructively at the two points in time separated by T in the upper part of the illustration 900. They cancel by destructive interference everywhere else in the time domain. For example, the mode n would occur at an optical frequency of 30,000 GHz, the mode n+1 occurs at 30,100 GHz, the mode n+2 occurs at 30,200 GHz, etc., and the mode n−1 occurs at 29,900 GHz, the mode n−2 occurs at 29,800 GHz, etc.

Figure 10:
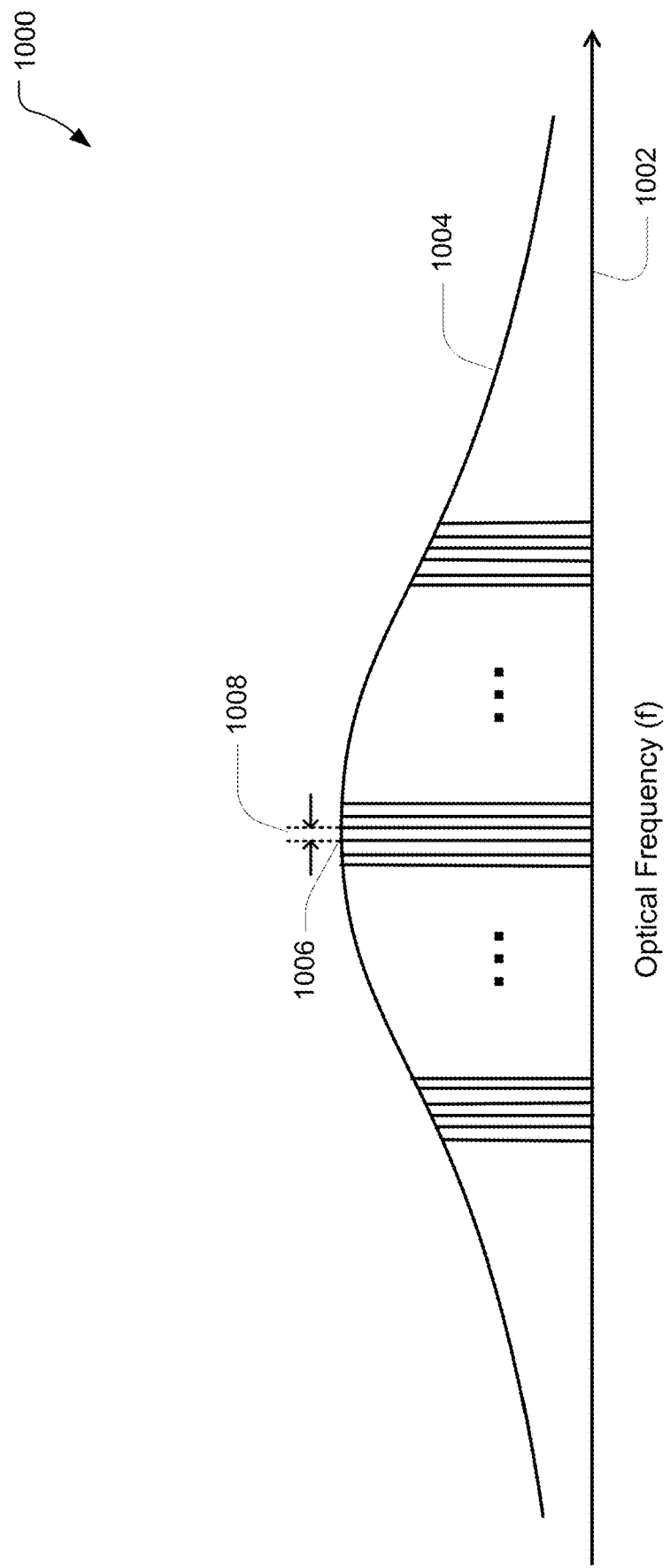
FIG. 10 illustrates an example of laser pulses in a laser frequency comb.

Referring to FIG. 10, an illustration 1000 of laser pulses in a laser frequency comb is shown. The illustration 1000 includes and optical frequency axis 1002, a mode intensity envelope 1004, a central mode frequency 1006, and a pulse repetition rate 1008. In an example, the central mode frequency 1006 may occur at 30,000 GHz (with photon energy of 1000.69 $cm^{-1}$) and the pulse repetition rate 1008 may be 100 GHz. Thus, the next higher mode may occur at an interval equal to the pulse repetition rate 1008 (e.g., 30,100 GHz with a photon energy of 1004.03 $cm^{-1}$), and the next higher mode occurs at 30,200 GHz (1007.36 $cm^{-1}$), etc. The mirror image sequence will occur on the other side of the 30,000 GHz mode (e.g., 29,900 GHz/997.36 $cm^{-1}$, 29,800 GHz/994.02 $cm^{-1}$, etc. . . . ). The result is an optical frequency comb as shown in FIG. 10, with a mode intensity envelope 1004 that tapers towards zero on both sides of the central 30,000 GHz optical frequency as shown, with an effective bandwidth exceeding one octave (factor of 2 in optical frequency).

Continuing the example, the separation between adjacent modes is approximately 3.3 $cm^{-1}$. This would serve as the spectral resolution limit of this particular frequency comb. To attain a spectral resolution of, for example, 0.33 cm-1, which is desirable for achieving a resolution that is adequate for measuring the spectral absorption of THC and related cannabinoid compounds, it would be necessary to achieve a factor of 10 lower mode locked pulse frequency of ~10 GHz. In that case, the separation between laser modes in FIG. 10 would be 0.33 cm-1. Even higher resolution would result if the mode locked pulse frequency is further reduced.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered. Accordingly, the above description does not bound the scope of the claims.

Other examples and implementations are within the scope and spirit of the disclosure and appended claims. For example, due to the nature of software and computers, functions described above can be implemented using software executed by a processor, hardware, firmware, hardwiring, or a combination of any of these. Features implementing functions may also be physically located at various positions, including being distributed such that portions of functions are implemented at different physical locations.

Also, as used herein, "or" as used in a list of items prefaced by "at least one of" or prefaced by "one or more of" indicates a disjunctive list such that, for example, a list of "at least one of A, B, or C," or a list of "one or more of A, B, or C," or "A, B, or C, or a combination thereof" means A or B or C or AB or AC or BC or ABC (i.e., A and B and C), or combinations with more than one feature (e.g., AA, AAB, ABBC, etc.).

As used herein, unless otherwise stated, a statement that a function or operation is "based on" an item or condition means that the function or operation is based on the stated item or condition and may be based on one or more items and/or conditions in addition to the stated item or condition.

Further, an indication that information is sent or transmitted, or a statement of sending or transmitting information, "to" an entity does not require completion of the communication. Such indications or statements include situations where the information is conveyed from a sending entity but does not reach an intended recipient of the information. The intended recipient, even if not actually receiving the information, may still be referred to as a receiving entity, e.g., a receiving execution environment. Further, an entity that is configured to send or transmit information "to" an intended recipient is not required to be configured to complete the delivery of the information to the intended recipient. For example, the entity may provide the information, with an indication of the intended recipient, to another entity that is capable of forwarding the information along with an indication of the intended recipient.

Substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations provides a description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, some operations may be performed in parallel or concurrently. In addition, the order of the operations may be rearranged. A process may have additional stages or functions not included in the figure. Furthermore, examples of the methods may be implemented by hardware, software, firmware, middleware, microcode, hardware description languages, or any combination thereof. When implemented in software, firmware, middleware, or microcode, the program code or code segments to perform the tasks may be stored in a non-transitory computer-readable medium such as a storage medium. Processors may perform one or more of the described tasks.

Components, functional or otherwise, shown in the figures and/or discussed herein as being connected, coupled (e.g., communicatively coupled), or communicating with each other are operably coupled. That is, they may be directly or indirectly, wired and/or wirelessly, connected to enable signal transmission between them.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of operations may be undertaken before, during, or after the above elements are considered. Accordingly, the above description does not bound the scope of the claims.

Further, more than one invention may be disclosed.

The invention claimed is:

1. A method of sensing a narcotic in exhaled breath, comprising:
   receiving a breath input from a test subject with a filter material;
   disposing the filter material including the breath input in an optical path between a laser source and a photodetector, wherein the laser source is an optical frequency comb laser with a separation of laser modes of 0.33 $cm^{-1}$ or less;
   detecting an intensity of infrared light that traverses the filter material including the breath input with the photodetector;
   determining one or more spectral absorption lines associated with the narcotic based on the intensity of the infrared light as a function of photon energy;
   determining a narcotic concentration value based on the one or more spectral absorption lines; and
   outputting the narcotic concentration value.

2. The method of claim 1 wherein receiving the breath input from the test subject includes providing the test subject a breath sampler device comprising a tube and the filter material.

3. The method of claim 1 wherein the narcotic is tetrahydrocannabinol (THC) and the one or more spectral absorption lines associated with THC includes a spectral absorption line at approximately 1036.94 $cm^{-1}$.

4. The method of claim 1 wherein the narcotic is oxycodone and the one or more spectral absorption lines associated with oxycodone are approximately between 700-1500 $cm^{-1}$.

5. The method of claim 1 wherein the narcotic is fentanyl and the one or more spectral absorption lines associated with fentanyl are approximately between 600-1500 $cm^{-1}$.

6. The method of claim 1 wherein the narcotic is morphine and the one or more spectral absorption lines associated with morphine are approximately between 600-1130 $cm^{-1}$.

7. The method of claim 1 wherein the narcotic is tetrahydrocannabinol (THC) and the one or more spectral absorption lines associated with THC are approximately between 600-1700 $cm^{-1}$.

8. The method of claim 1 wherein the one or more spectral absorption lines includes one or more spectral absorption lines known to be associated with Cannabidiol (CBD).

9. An apparatus for sensing a narcotic in an exhaled breath, comprising:
   an optical frequency comb laser with a separation of laser modes of 0.33 $cm^{-1}$ or less;
   at least one photodetector;
   a sample cell disposed between the optical frequency comb laser and the at least one photodetector, wherein the sample cell includes an aerosol obtained from the exhaled breath; and
   at least one processor operably coupled to the optical frequency comb laser and the at least one photodetector and configured to:
   provide a control signal to the optical frequency comb laser;
   determine one or more spectral absorption lines associated with the narcotic based on an intensity of infrared light detected by the at least one photodetector; and
   determine a narcotic concentration value based on the spectral absorption lines.

10. The apparatus of claim 9 further comprising a breath sampler device including a tube operably coupled to the filter material that is configured to receive a breath input from a test subject.

11. The apparatus of claim 9 wherein the at least one processor is configured to determine the one or more spectral absorption lines is associated with THC as approximately 1036.94 cm$^{-1}$.

12. The apparatus of claim 9 wherein the at least one processor is configured to determine the one or more spectral absorption lines known to be associated with THC.

13. The apparatus of claim 9 wherein the narcotic is oxycodone and the at least one processor is configured to determine the one or more spectral absorption lines associated with oxycodone are approximately between 700-1500 cm$^{-1}$.

14. The apparatus of claim 9 wherein the narcotic is fentanyl and the at least one processor is configured to determine the one or more spectral absorption lines associated with fentanyl are approximately between 600-1500 cm$^{-1}$.

15. The apparatus of claim 9 wherein the narcotic is morphine and the at least one processor is configured to determine the one or more spectral absorption lines associated with morphine are approximately between 600-1130 cm$^{-1}$.

16. An apparatus for sensing a narcotic in an exhaled breath, comprising:
   an optical frequency comb laser;
   at least one photodetector;
   a filter material disposed between the optical frequency comb laser and the at least one photodetector, wherein the filter material includes an aerosol obtained from the exhaled breath;
   at least one processor operably coupled to the optical frequency comb laser and the at least one photodetector and configured to:
      pulse the optical frequency comb laser at a mode lock pulse frequency of approximately 10 Gigahertz or less and a separation between laser modes of 0.33 cm$^{-1}$ in a mode locked condition;
      determine one or more spectral absorption lines associated with the narcotic based on an intensity of infrared light detected by the at least one photodetector; and
      determine a narcotic concentration value based on the spectral absorption lines.

* * * * *